United States Patent
Werner et al.

(10) Patent No.: US 8,044,354 B2
(45) Date of Patent: Oct. 25, 2011

(54) METHOD FOR CLASSIFYING RESINS TYPES IN CARBON FIBER REINFORCED PLASTIC MATERIALS USING IR SPECTROSCOPY

(75) Inventors: Gregory J. Werner, Puyallup, WA (US); Paul H. Shelley, Lakewood, WA (US); Panagiotis E. George, Lake Tapps, WA (US)

(73) Assignee: The Boeing Company, Chicago, IL (US)

( * ) Notice: Subject to any disclaimer, the term of this patent is extended or adjusted under 35 U.S.C. 154(b) by 426 days.

(21) Appl. No.: 12/327,826

(22) Filed: Dec. 4, 2008

(65) Prior Publication Data

US 2010/0140476 A1    Jun. 10, 2010

(51) Int. Cl.
*G01J 5/02* (2006.01)

(52) U.S. Cl. ......... 250/339.11; 250/339.07; 250/339.08; 250/339.12; 250/340; 250/341.1; 250/341.8

(58) Field of Classification Search ............. 250/339.07, 250/339.08, 339.12, 340, 341.1, 341.8, 339.11
See application file for complete search history.

(56) References Cited

U.S. PATENT DOCUMENTS

| | | | |
|---|---|---|---|
| 5,510,619 A * | 4/1996 | Zachmann et al. | 250/339.08 |
| 5,952,660 A * | 9/1999 | Kip et al. | 250/339.11 |
| 6,184,528 B1 * | 2/2001 | DiMarzio et al. | 250/339.08 |
| 7,145,147 B1 | 12/2006 | Shelley et al. | |
| 2010/0267868 A1 * | 10/2010 | Takahashi et al. | 524/79 |

* cited by examiner

*Primary Examiner* — David Porta
*Assistant Examiner* — Christine Sung
(74) *Attorney, Agent, or Firm* — Tung & Associates

(57) ABSTRACT

In one embodiment, a method of classifying a polymer containing surface is provided including collecting one or more spectra of infrared energy reflected from the surface over a spectrum of wavelengths; performing multivariate processing at one or more wavelengths; comparing results of the multivariate processing with one or more predetermined material classification models derived from model material infrared energy spectra collected from one or more model material surfaces, the one or more model material surfaces each having a known polymer material composition; and, sorting the polymer containing surface into the proper class based on a similarity of the results of the multivariate processing at one or more wavelengths with the predetermined material classification models.

20 Claims, 3 Drawing Sheets

METHOD FOR CLASSIFYING RESINS TYPES IN CARBON FIBER REINFORCED PLASTIC MATERIALS USING IR SPECTROSCOPY

TECHNICAL FIELD

The disclosure generally relates to Infrared (IR) spectroscopy measurement methods and apparatus, and more particularly provides a method and IR spectrometer for performing non-destructive IR spectroscopy measurements of resins in carbon fiber reinforced plastic (CFRP) materials in order to classify resin types associated with the CFRP material.

BACKGROUND

IR spectroscopy measurements may be useful for a variety of purposes including aerospace, automotive and industrial applications, as well as biological and bio-medical applications. For example, infrared (IR) radiation is readily absorbed by materials in association with relative motions (vibrations) of bonds between common atoms such as carbon, hydrogen, oxygen and nitrogen. As such, IR spectroscopy measurements may indicate a condition and/or identity of a wide variety of organic as well as inorganic materials.

Polymer composite materials such as fiber-resin-based materials including carbon fiber reinforced plastic composite materials have been widely used for a variety of purposes including as a structural material. Increasingly, it is desirable to recycle polymer materials including polymer composite materials.

In performing recycling processes, it is first desirable to know the chemical make-up or resin type of a particular CFRP composite material. For example, subsequent processing steps including optimal heat treatments may depend on the particular resin system.

Prior art methods for determining chemical properties of a resin material such as commonly owned U.S. Pat. No. 7,145,147, which is hereby incorporated by reference in its entirety, include using optical interfaces such as filters and ATR crystals positioned on a sample surface to determine a normalized TR absorbance of sample material. In addition, a relatively bulky IR spectrometer is useable where the source and the detector are separately positioned to make an IR measurement, such as in a controlled environment.

While the prior art methods and TR apparatus may be desirably useable in a controlled environment where IR absorbance is separately collected and compared in a relatively time-consuming process, it would be additionally desirable to make IR spectroscopy measurements in a relatively quick and simple manner in a field setting.

Accordingly there is a need for a method for making IR spectroscopy measurements and an IR spectrometer that overcomes at least some of the drawbacks of prior art including making IR spectroscopy field measurements in a relatively quick and simple manner.

SUMMARY

A portable hand-held IR spectrometer is provided that that may be used to make field IR spectroscopic measurements subjected to multivariate analysis in near real time in order to classify a polymer material, including determining chemical properties of a resin including a resin-type present a CFRP composite material. The method may be used in the context of sorting recycled CFRP composite materials in a recycling process to optimize a temperature treatment step.

In one exemplary embodiment, a method of identifying a polymer containing surface is provided including collecting one or more spectra of infrared energy reflected from the surface over a spectrum of wavelengths; performing multivariate processing at one or more wavelengths; comparing results of the multivariate processing with one or more predetermined material classification models derived from model material infrared energy spectra collected from one or more model material surfaces, the one or more model material surfaces each having a known polymer material composition; and, classifying the polymer containing surface based on a similarity of the results of the multivariate processing at one or more wavelengths with the predetermined material classification models.

In another exemplary embodiment the polymer material includes a resin-based composite material and the method includes a recycling process including the steps of: determining a subsequent temperature processing step based on said classification of said polymer containing surface; and, heating said resin-based composite material at a sufficient time and temperature to incinerate said resin.

In another exemplary embodiment a method of identifying a resin-based composite material with a portable hand-held IR spectrometer is provided, the method including: irradiating the resin-based composite material with infrared energy over a spectrum of wavelengths; collecting one or more spectra of the infrared energy reflected from the resin-based composite material over the spectrum of wavelengths; performing multivariate processing at one or more wavelengths including the one or more infrared spectra; comparing results of the multivariate processing with one or more predetermined material classification models derived from model material infrared energy spectra collected from one or more model materials, the one or more model materials each including a known resin-based composite material composition; and, classifying the resin-based composite material based on a similarity of said results of said multivariate processing at one or more wavelengths with the predetermined material classification models; wherein the steps of irradiating, collecting, performing, comparing and classifying are accomplished with the portable hand-held spectrometer.

BRIEF DESCRIPTION OF THE ILLUSTRATIONS

Exemplary embodiments will become more fully understood from the detailed description and the accompanying drawings, wherein.

DETAILED DESCRIPTION

The following detailed description is merely exemplary (illustrative) in nature and is not intended to limit the described embodiments or the application and the uses of the described embodiments. Furthermore, there is no intention to be bound by any expressed or implied theory presented in the disclosure.

A method of non-destructively determining a chemical classification of a polymer material is provided, such as the identification (classification) of a resin-based polymer composite material where the method may be accomplished by making an infrared (IR) spectroscopy measurement with an IR spectrometer, preferably a portable hand-held FT-IR spectrometer. Multivariate classification methods may be used to classify (identify one or more chemical ingredients) resin-based polymer composite materials, including as part of a recycling process.

It will be appreciated that although the IR spectroscopy methods and apparatus may be used to classify a resin-based composite material according to its chemical make-up in the context of a recycling process, that the chemical identification and classification process may be used in any process where such process may be desirably be conducted in the field by a portable hand-held IR spectrometer to make a relatively quick measurement and determination in near-real time of a polymer material.

It will be appreciated that either a portable or non-portable IR spectrometer may be used to carry out IR spectroscopy measurements according to exemplary embodiments, and the spectrum of wavelengths used to make the IR spectroscopy measurements may include all or a portion of the wavelengths between about 2.5 to 15.4 microns (4000 to 650 wavenumbers (cm−1).

In an exemplary embodiment, a hand-held portable IR spectrometer capable of performing Fourier transform infrared (FT-IR) spectroscopy measurements is used to perform the IR spectroscopy measurements The hand-held portable FT-IR spectrometer preferably has the capability to supply source IR energy to a sample at a predetermined incident angle between about 30 to about 60 degrees, most preferably 45 degrees, and collect reflected light from the sample through a broad range of angles including the incident angle. The hand-held portable FT-IR device preferably has the ability to make specular-diffuse reflectance IR spectroscopic measurements.

In another exemplary embodiment, a portable hand-held IR spectrometer capable of making diffuse reflectance IR measurements over the near infrared wavelength range (700-2400 nm) may be used to make the IR spectroscopy measurements.

Figure 1:
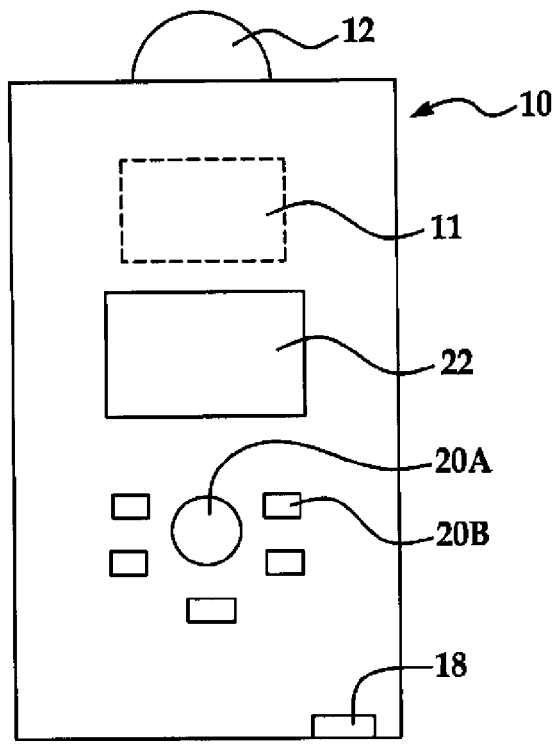
FIG. 1 is a schematic diagram of an exemplary hand-held portable IR spectrometer suitably used to make IR spectroscopy measurements according to exemplary embodiments.

Referring to FIG. 1 is shown a top view of a hand-held portable IR spectrometer 10 according to an exemplary embodiment. The portable IR spectrometer 10 may have the capability of performing either FT-IR or near infrared TR spectroscopy measurements, but in a preferred embodiment at least has the capability of performing FT-IR spectroscopy measurements. By the term 'hand-held' is meant an instrument that may be easily carried and picked up and move about to make IR spectroscopy measurements by an average person, e.g., has a weight of less than about 8 pounds and a size of less than about 1 ft by 1 ft.

In another exemplary embodiment, the hand-held portable FT-IR spectrometer 10 shown in FIG. 1 is capable of performing FT-IR spectroscopy measurements over a wavelength range of about 2.5 to 15.4 microns or 4000 to 650 wavenumbers (cm−1).

The hand-held portable IR spectrometer 10 may include a computer processor and memory (e.g., 11) and may be interfaced (placed in communicated with) with other computing devices (e.g., USB port 18). The hand-held portable IR spectrometer 10 may be supplied power by one or more batteries. The hand-held portable IR spectrometer 10 may be programmable and/or capable of accepting, storing, and executing preprogrammed instructions for carrying out FT-IR spectroscopy measurements. The hand-held portable IR spectrometer 10 further may have the capability to provide incident IR light (energy) and collect and store in memory reflected IR spectra (e.g., through one or more IR transparent energy windows/domes e.g., 12) over an operating wavelength range (e.g., 2.5 to 15.4 microns).

For example the incident IR energy may be provided at various incident angles to a sample and collected over a broad range of wavelengths including an incident angle. The hand-held portable IR spectrometer 10 may have the ability to store collected IR spectra and perform mathematical manipulation of the data comprising the IR spectra including performing multivariate methods to process the spectra. The hand-held portable IR spectrometer 10 may include interactive buttons e.g., 20A, 20B, and/or softkeys on an interactive LCD or LED touchscreen 22. It will be appreciated that the hand-held portable IR spectrometer 10 may be of any suitable ergonomic shape to enhance the portability and ease of holding and manipulating the spectrometer to carryout IR spectroscopy measurements in the field.

In addition, suitable calibration background reference standard materials and wavelength reference standard materials may be provided for calibrating the IR spectrometer 10 prior to performing IR spectroscopy measurements according to exemplary embodiments.

The hand-held portable IR spectrometer 10, or another IR spectrometer used to carry out IR spectroscopy measurements according to embodiments, preferably includes a computer processor capable of multivariate analysis of the IR spectra. For example, the IR spectrometer (or an associated controller) preferably has the ability to mathematically and statistically correlate and determine changes in a plurality of variables e.g., IR spectra including reflectance and/or absorbance at a plurality of wavelengths.

For example, multivariate statistical approaches may be used to correlate the statistically determined relative changes in the plurality of variables (e.g., relative changes in absorbance and/or reflectance at one or more wavelengths) is correlated with one or more second variables or (e.g. a change in a separately determined material property (e.g., one or more chemical compositions).

There are many suitable multivariate classification techniques that may be used with IR spectral data according to embodiments including, but not limited to, quantification methodologies, such as, partial least squares, principal component analysis (PCA) or principle component regression (PCR), linear regression, multiple linear regression, stepwise linear regression, ridge regression, radial basis functions, and the like.

In addition, suitable multivariate statistical approaches may include additional classification methodologies, such as, linear discriminant analysis ("LDA"), cluster analysis (e.g., k-means, C-means, etc., both fuzzy and hard), and neural network ("NN") analysis.

Further, it will be appreciated that there are several data processing methods that may be suitably used to in connection with suitable multivariate statistical approaches including smoothing, normalization, taking of first and second derivatives of the raw IR spectra, and peak enhancement methods.

In addition, multivariate processing of collected IR spectra may include the selection and clustering together of groups of wavelengths on which to perform a regression analysis to determine a corresponding change in the IR spectra (e.g., reflectance and/or absorbance) with respect to reference spectra. It will be appreciated that a processed IR spectrum may be formed from several raw IR spectra (e.g., by multiple scans over a wavelength range and using averaging techniques known in the art).

The raw IR spectra may further be transformed into second IR spectra by taking first and/or second derivatives and performing smoothing and/or peak enhancement as well as carrying out regression analysis. For example, manipulation the raw IR spectra by smoothing algorithms prior to or following taking a first derivative may be performed.

In one exemplary embodiment, an IR spectrometer used to carry out an IR spectroscopy measurement according to embodiments, such as the portable IR spectrometer 10, may be provided and have stored in memory one or more material classification models including the results of one or more multivariate classification methods applied to exemplary reference (model) polymer materials including CFRP composite materials. The material classification models are used to compare in near real time with sample spectra taken in the field with the handheld portable spectrometer to determine whether there is a an acceptable correlation or match to a particular material classification model. It will be appreciated that the chemical composition and/or a determination of a resin type present in the model materials may be separately determined, including referring to or carrying out a separate chemical analysis.

For example, as further outlined below, the raw IR spectra of reference samples may be collected by a similar or different IR spectrometer and subjected to multivariate analysis to create material classification models for different types of resin-based polymer composite materials. In an exemplary embodiment, one or more of the classification models are then stored in memory in the hand-held portable IR spectrometer 10.

IR spectra of sample resin-based composite materials are then collected by the hand-held portable IR spectrometer e.g., 10 and subjected to a near-real-time multivariate analysis of the sample similar to that performed on the reference samples. A resulting classification (match or no match) with respect to one or more of the classification models of the reference resin-based materials may then be made in near-real-time by the hand-held portable IR spectrometer e.g., 10. In this manner, a positive classification of the type of CFRP composite material may be made.

In an exemplary process, a hand-held portable FT-IR spectrometer, similar to hand-held spectrometer 10 was used to carry out 5 IR spectroscopy measurements (readings) each on 6 different CFRP composite materials and their IR signatures (multivariate processed spectra) examined to sort them as different materials.

Figure 2A:
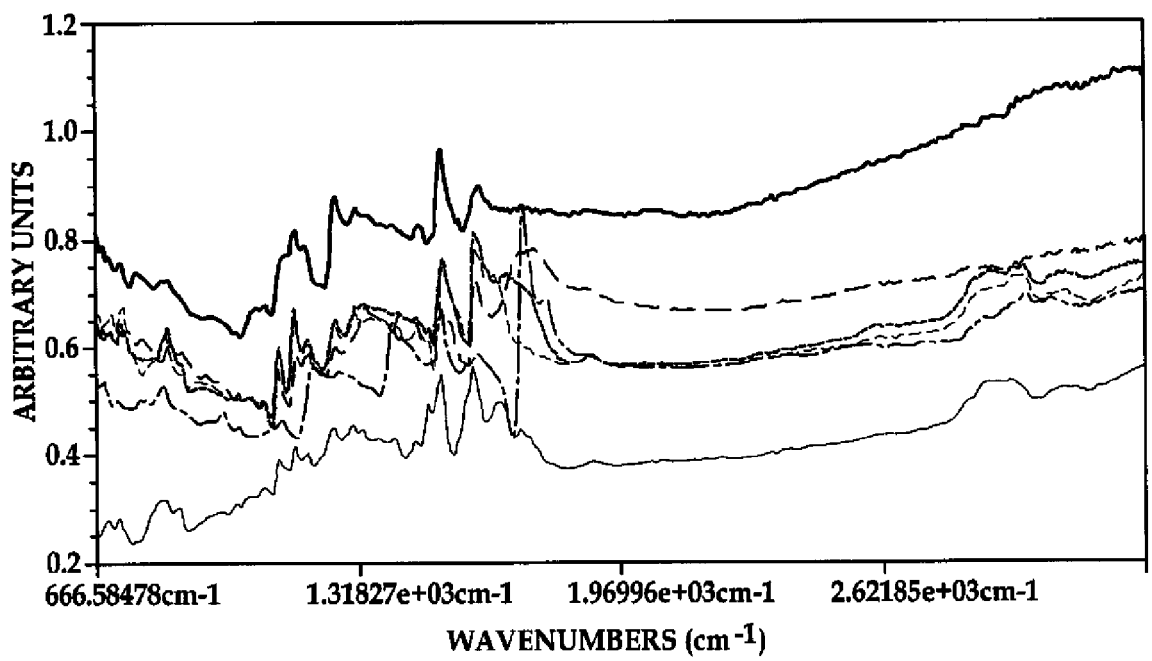
FIG. 2A shows exemplary IR spectra of different resin-based composite material samples over a selected IR wavelength range.

For example, referring to FIG. 2A, is shown exemplary raw data (e.g., absorbance) for each of the 6 different resin-based composite materials (panels), collected over a mid-IR range of wavelengths where 128 scans with 8 cm$^{-1}$ resolution were made for each 'reading' associated with a respective panel.

Figure 2B:
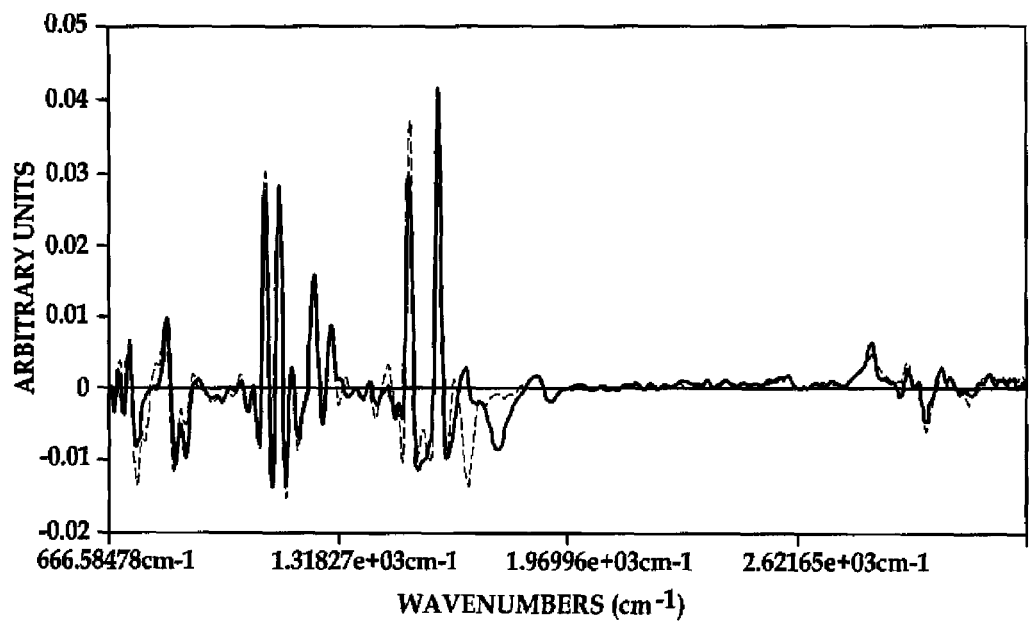
FIG. 2B show exemplary IR spectra of different resin-based composite material samples following partial multivariate data processing according to exemplary embodiments.

Referring to FIG. 2B, are shown the most similar panels (1 and 5) plotted together following taking a $1^{st}$ derivative and applying a smoothing algorithm to the data using 7 smoothing points. Several of the peaks show significant differences despite the similarity of the raw IR data.

Figure 2C:
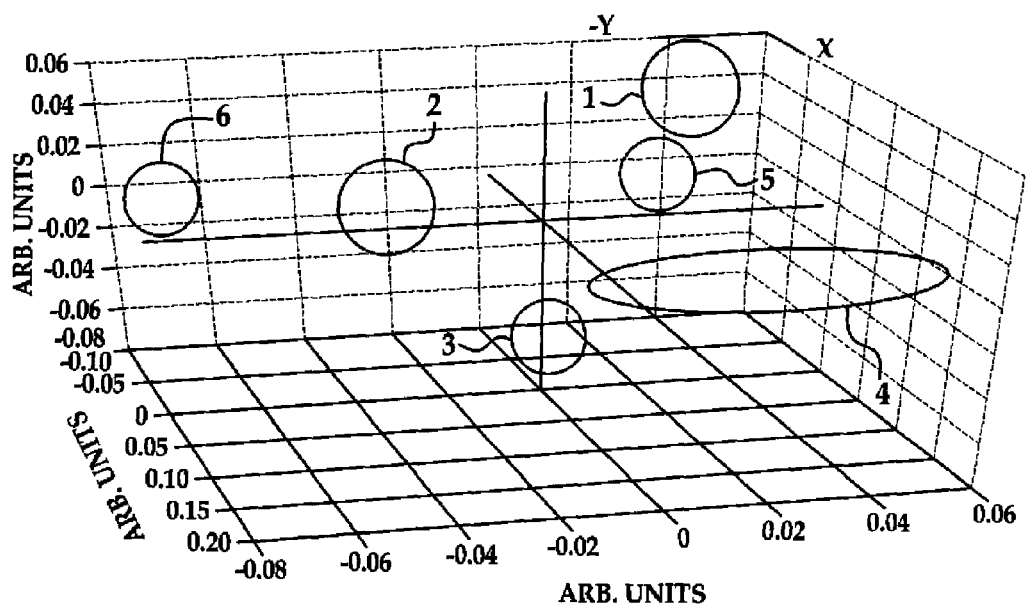
FIG. 2C shows show exemplary results of different resin-based composite materials following further multivariate data processing according to exemplary embodiments.

Referring to FIG. 2C, is shown a 3-dimensional plot following an exemplary three principle component (3-PC) analysis (PCA), also referred to as a 3-PC regression (PCR). It is seen that panels 1 and 5 show the smallest separation, whereas panel 4 shows scatter, believed to be due to surface roughness. It is noted that applying 2 PC model was found to be insufficient to separate the two similar materials in panels 1 and 5.

Thus, the numerical space represented by spheres (shown as circles) surrounding the various panels of material shown in FIG. 2C may be defined as a matching numerical domain to identify an unknown resin-based composite material including carbon fiber reinforced resin composites (also referred to as CFRP), or polymer materials in general. For example, if an unknown material falls on and/or within the model material domain space (e.g., sphere) following similar multivariate processing steps (e.g., $1^{st}$ derivative, 7 smoothing points, 3 PCA), the hand-held spectrometer may be programmed to report a match or classification corresponding to the model material.

In an exemplary embodiment, the time to take an IR spectroscopy measurement including the time to identify a material type may take from about 5 seconds to about 90 seconds, more preferably from about 10 seconds to about 60 seconds.

It will be appreciated that in making a particular IR spectroscopy measurement or establishing classification models for reference samples, the same or different measurement parameters may be used. For example, the number of scans taken (e.g., each scan over a predetermined range of wavelengths) and where the scans are averaged, may vary. In addition, the number of 'readings' taken on a respective material sample may vary. Preferably, however, the multivariate data processing steps (e.g., $1^{st}$ derivate and 7 smoothing points) for the unknown sample and the classification models are substantially similar.

Further, in some embodiments, the orientation of the hand-held IR spectrometer with respect to a resin may be a factor when making an IR spectroscopy measurement. For example, it may be preferable, depending on the type of composite material, that the incident IR energy be provided at an orientation perpendicular to a composite fiber direction e.g., in composite fiber-resin material, such as carbon fiber reinforced material also referred to as carbon fiber reinforced polymer (CFRP).

In some embodiments, a composite material surface e.g., resin-based composite material such CFRP, may include an organic surface finishing product, such as an epoxy. Thus, it will be appreciated that reference herein to a resin-based composite material may further include the presence of a coating of an organic material on the surface.

Figure 3:
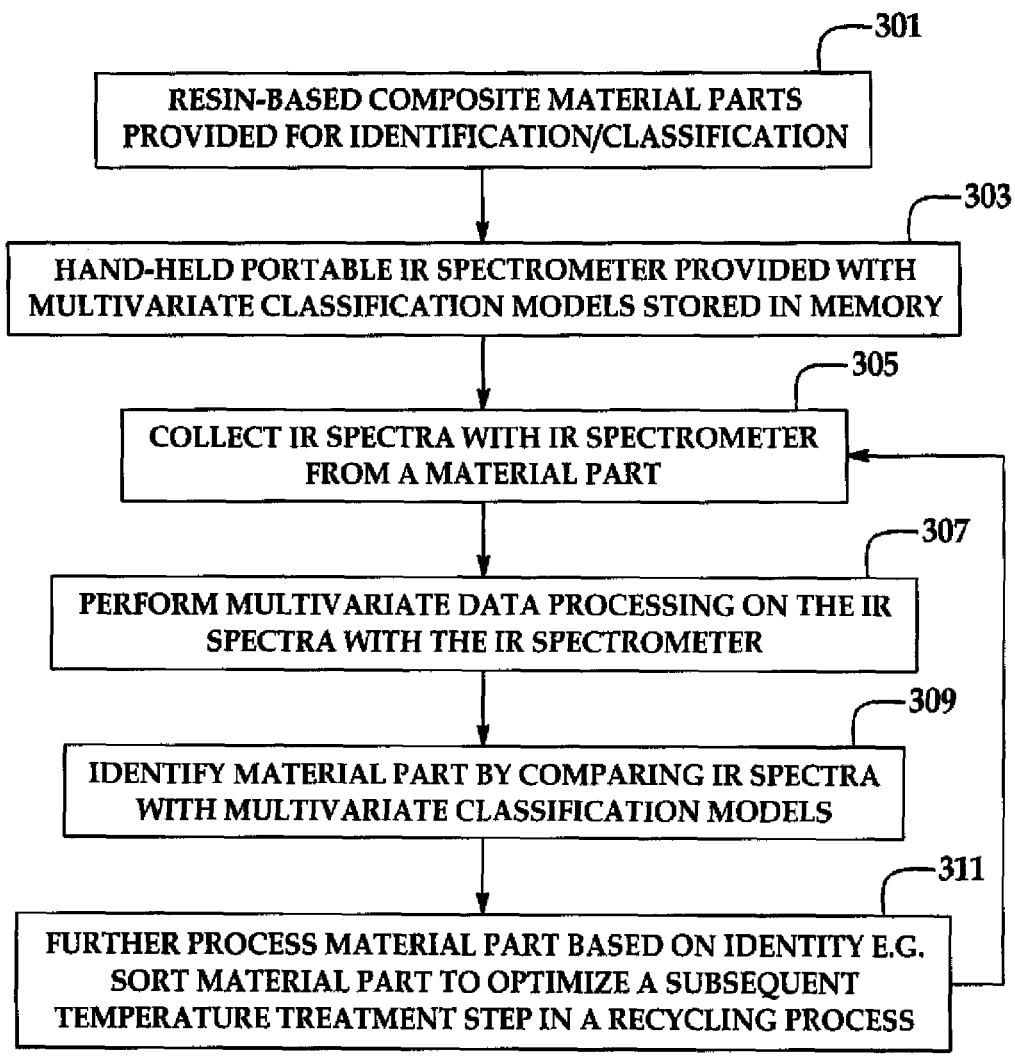
FIG. 3 shows an exemplary process flow according to an exemplary embodiment using a portable handheld IR spectrometer.

Referring to FIG. 3 is shown an exemplary process using a hand-held IR spectrometer e.g., 10, to make an IR classification (identification of one or more chemical ingredients) of an unknown resin-based composite material according to an exemplary embodiment.

In block 301, an unknown plurality of resin-based composite parts with an unknown resin type are provided for classification/identification (e.g., in a recycle operation). In block 303, a hand-held spectrometer, e.g., 10 is provided with one or more IR material classification models (multivariate classification models) stored in memory. In block 305 one or more IR spectroscopy measurements to collect raw IR data are made with the hand-held spectrometer on a material of the part. In block 307, multivariate processing is carried out on the raw data with the IR spectrometer. In block 309, the material of the part is identified with the IR spectrometer as a particular type of resin-based composite material (matching a material model). In block 311, the part is then further processed (e.g., sorted into an appropriate processing bin for further recycling steps). The process may begin again with another resin-based composite part in block 305.

For example, in an exemplary embodiment, the identification of resin-based composite parts using the hand-held spectrometer according to classification models, is made in order to determine the resin type a particular resin-based composite material may contain. For example, recycling of resin-based composite materials relies on knowing the type of resin that is present in order to determine appropriate subsequent processing steps, such as optimizing furnace processing conditions used to treat the material to optimize material recovery.

In an exemplary process, the resin-based composite material includes carbon fibers (such as CRFP) where the resin is burned off (incinerated) to recover the carbon fibers for re-use by known processes. The appropriate incineration temperature may depend on the resin type included in the composite material.

For example, a series of sorting bins may be established in a recycle operation whereby the hand-held portable IR spectrometer with predetermined material classification models is used to identify a resin type in a resin-based composite material. Following identification of a resin type, the material of the part may be appropriately sorted e.g., into respective sorting bins in preparation for a next step, such as furnace processing.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A method of identifying a polymer containing surface on a resin-based composite material comprising:
   irradiating said polymer containing surface with infrared energy over a spectrum of wavelengths;
   collecting one or more spectra of said infrared energy reflected from said surface over said spectrum of wavelengths;
   performing multivariate processing at one or more wavelengths comprising the one or more infrared spectra;
   comparing results of said multivariate processing with one or more predetermined material classification models derived from model material infrared energy spectra collected from one or more model material surfaces, said one or more model material surfaces each comprising a known polymer material composition;
   identifying said polymer containing surface based on a similarity of said results of said multivariate processing at one or more wavelengths with said predetermined material classification models;
   determining a subsequent temperature processing step based on said identifying said polymer containing surface; and,
   heating said resin-based composite material at a sufficient time and temperature to incinerate said resin.

2. The method of claim 1, wherein said multivariate processing of said one or more infrared spectra comprises selected spectral peaks of said one or more infrared spectra.

3. The method of claim 1, wherein said polymer comprises a resin-based material.

4. The method of claim 1, wherein said polymer comprises a resin-based composite material.

5. The method of claim 1, wherein said polymer comprises a carbon reinforced fiber resin-based composite material.

6. The method of claim 1, wherein said spectrum of wavelengths is from about 2.5 and about 16.7 microns.

7. The method of claim 1, wherein said steps are performed by a hand-held portable IR spectrometer.

8. The method of claim 7, wherein said hand-held portable IR spectrometer has the ability to make Fourier transform IR spectroscopic measurements.

9. The method of claim 1, wherein said multivariate processing comprises at least one of taking a derivative, applying a smooth algorithm, and performing a principle component regression.

10. The method of claim 1, wherein said resin-based composite material comprises carbon fibers and said method further comprises the step of:
    collecting said fibers for re-use following said incineration.

11. A method of identifying a resin-based composite material comprising:
    irradiating said resin-based composite material with infrared energy over a spectrum of wavelengths;
    collecting one or more spectra of said infrared energy reflected from said resin-based composite material over said spectrum of wavelengths;
    performing multivariate processing at one or more wavelengths comprising the one or more infrared spectra;
    comparing results of said multivariate processing with one or more predetermined material classification models derived from model material infrared energy spectra collected from one or more model materials, said one or more model materials each comprising a known resin-based composite material composition;
    identifying said resin-based composite material based on a similarity of said results of said multivariate processing at one or more wavelengths with said predetermined material classification models;
    determining a subsequent temperature processing step based on said identifying said resin-based composite material; and,
    heating said resin-based composite material at a sufficient time and temperature to incinerate said resin.

12. The method of claim 11, wherein said multivariate processing of said one or more infrared spectra comprises selected spectral peaks of said one or more infrared spectra.

13. The method of claim 12, wherein said resin-based composite material comprises a carbon reinforced fiber resin-based composite material.

14. The method of claim 12, wherein said spectrum of wavelengths is from about 2.5 and about 16.7 microns.

15. The method of claim 12, wherein said steps are performed by a hand-held portable IR spectrometer.

16. The method of claim 15, wherein said hand-held portable IR spectrometer has the ability to make Fourier transform IR spectroscopic measurements.

17. The method of claim 12, wherein said multivariate processing comprises at least one of taking a derivative, applying a smooth algorithm, and performing a principle component regression.

18. The method of claim 11, wherein said resin-based composite material comprises carbon fibers and said method further comprises the step of:
    collecting said fibers for re-use following said incineration.

19. A method of identifying a resin-based composite material with a portable hand-held IR spectrometer comprising:
    irradiating said resin-based composite material with infrared energy over a spectrum of wavelengths;
    collecting one or more spectra of said infrared energy reflected from said resin-based composite material over said spectrum of wavelengths;
    performing multivariate processing at one or more wavelengths comprising the one or more infrared spectra;
    comparing results of said multivariate processing with one or more predetermined material classification models derived from model material infrared energy spectra collected from one or more model materials, said one or more model materials each comprising a known resin-based composite material composition;

identifying said resin-based composite material based on a similarity of said results of said multivariate processing at one or more wavelengths with said predetermined material classification models; wherein said steps of irradiating, collecting, performing, comparing and identifying are accomplished with said portable hand-held spectrometer;

determining a subsequent temperature processing step based on said identifying said resin-based composite material; and, heating said resin-based composite material at a sufficient time and temperature to incinerate said resin.

20. The method of claim 19, further comprising collecting remaining carbon fibers following said incineration, said carbon fibers comprising said resin-based composite material.

* * * * *